United States Patent [19]

Enjouji et al.

[11] 4,407,709

[45] Oct. 4, 1983

[54] METHOD AND APPARATUS FOR FORMING OXIDE COATING BY REACTIVE SPUTTERING TECHNIQUE

[75] Inventors: Katsuhisa Enjouji; Hiroshi Ikeizumi, both of Nishinomiya; Kenji Murata, Takarazuka; Syozaburo Nishikawa, Itami, all of Japan

[73] Assignee: Nippon Sheet Glass Co., Ltd., Osaka, Japan

[21] Appl. No.: 363,777

[22] Filed: Mar. 31, 1982

[30] Foreign Application Priority Data

Mar. 31, 1981 [JP] Japan ................................ 56/48258

[51] Int. Cl.$^3$ .............................................. C23C 15/00
[52] U.S. Cl. ................................. 204/192 SP; 204/298
[58] Field of Search .......................... 204/192 SP, 298

[56] References Cited

U.S. PATENT DOCUMENTS 3,738,926  6/1973  Westwood et al. ................. 204/298
4,036,167  7/1977  Lu ....................................... 204/298
4,289,188  9/1981  Mizutani ............................. 204/298

OTHER PUBLICATIONS

Harshbarger et al., J. Electronic Mat. 7(1978), pp. 429-440.
Westwood, J. Appl. Phys. 44(1973), p. 2619-2626.
Westwood et al., J. Appl. Phys. 44(1973), pp. 2610-2618.
Ratinen, J. Applied Phys. 44(1973), pp. 2730-2734.
Greene et al., J. Applied Phys. 44(1973), pp. 2509-2513.
Greene et al., J. Vac. Sci. Technol. 10(1973), pp. 1144-1150.

*Primary Examiner*—Arthur P. Demers
*Attorney, Agent, or Firm*—Wenderoth, Lind & Ponack

[57] ABSTRACT

A method for forming a coating of an oxide on a support by the reactive sputtering technique, which comprises measuring the intensity of at least one spectral component having a given wavelength of the spectrum of a plasma formed between the support and a target composed of an oxidizable substance convertible to said oxide, comparing the measured intensity of the spectral component with the standard intensity of a spectral component of the same wavelength, and continuously or intermittently varying the physical amount of a sputtering gas and/or the amount of an electric current from a sputtering power supply so that the measured intensity of the former spectral component approaches the standard intensity of the latter spectral component; and a sputtering apparatus for performing the aforesaid method, which comprises a vacuum chamber, a target electrode disposed within the vacuum chamber, means for introducing a sputtering gas into the vacuum chamber, means for discharging the sputtering gas from the vacuum chamber, and a power supply for applying a negative voltage, an optical spectroscopic instrument for measuring the intensity of at least one component having a given wavelength of the spectrum of a plasma formed on the surface of the target electrodfe, and control circuit means for comparing the measured intensity of the spectral component with the standard intensity of a spectral component having the same wavelength.

15 Claims, 6 Drawing Figures

METHOD AND APPARATUS FOR FORMING OXIDE COATING BY REACTIVE SPUTTERING TECHNIQUE

This invention relates to a method and an apparatus for forming an oxide coating on a support by a reactive sputtering technique. More specifically, it pertains to a method and an apparatus which are suitable for forming a transparent or semi-transparent coating of an electrically conductive metal oxide on a transparent or semi-transparent support such as a glass or plastic plate.

Materials having various oxide coatings, especially coatings of electrically conductive metal oxides, are useful in various applications, and those having transparent or semi-transparent coatings have recently found extensive use as electrodes of liquid crystal display elements. A typical material usually employed as an electrode of a liquid crystal display element is a glass plate having a coating of a metal oxide comprising $SnO_2$ as a major component and $Sb_2O_3$ as a minor component or a glass plate having a coating of a metal oxide comprising $In_2O_3$ as a major component and $SnO_2$ as a minor component. The latter is especially preferred because it has high electric conductivity and high transparency and can be easily etched chemically with an acid. These materials having oxide coatings can be produced by depositing oxide coatings on supports by a sputtering technique, a vacuum evaporation technique, etc.

The reactive sputtering technique has the advantage of being able to form an oxide coating on a support having a large area. The reactive sputtering technique is a process which comprises placing a support in a vacuum chamber having an oxidizable substance convertible to an oxide as a target (cathode), the support being located opposite the target; introducing a sputtering gas containing molecular oxygen into the vacuum chamber; and then applying a negative voltage to the target to generate a plasma between the target and the support, thereby depositing an oxide coating on the support.

It has previously been difficult to form an oxide coating having a uniform thickness, uniform properties, etc. by the reactive sputtering process because conventional methods for forming oxide coatings by the reactive sputtering technique have been performed by adjusting a discharge electric power, etc. on the basis of the macroscopically determined amount of the plasma.

It is an object of this invention to provide a method for forming an oxide coating having a uniform thickness, uniform properties, etc. on a support or substrate by the reactive sputtering technique.

Another object of this invention is to provide a method for forming an oxide coating having a uniform thickness, uniform properties, etc. on a support at a high and controlled speed by the reactive sputtering technique.

Still another object of this invention is to provide a method for forming an oxide coating by the reactive sputtering technique while controlling the physical amount of a sputtering gas and/or the amount of an electric current from a sputtering power supply.

A further object of this invention is to provide a sputtering apparatus suitable for practicing the method of this invention comprising control circuit means for controlling the physical amount of a sputtering gas and/or the amount of an electric current from a sputtering power supply.

Other objects and advantages of this invention will become apparent from the following description.

These objects and advantages are achieved in accordance with this invention by a method for forming a coating of an oxide on a support by the reactive sputtering technique, characterized by comprising measuring the intensity of at least one spectral component having a given wavelength of the spectrum of a plasma formed between the support and a target composed of an oxidizable substance convertible to said oxide, comparing the measured intensity of the spectral component with the standard intensity of a spectral component of the same wavelength, and continuously or intermittently varying the physical amount of a sputtering gas and/or the amount of an electric current from a sputtering power supply so that the measured intensity of the former spectral component approaches the standard intensity of the latter spectral component.

According to this invention, the above method can be advantageously performed by a sputtering apparatus comprising a vacuum chamber, a target electrode disposed within the vacuum chamber, means for introducing a sputtering gas into the vacuum chamber, means for discharging the sputtering gas from the vacuum chamber, and a power supply for applying a negative voltage to the target electrode, characterized by including an optical spectroscopic instrument for measuring the intensity of at least one component having a given wavelength of the spectrum of a plasma formed on the surface of the target electrode, and control circuit means for comparing the measured intensity of the spectral component with the standard intensity of a spectral component having the same wavelength and when there is a difference between the two, varying the physical amount of the sputtering gas and/or the amount of an electric current from the sputtering power suply so that the measured intensity approaches the standard intensity.

The invention is further described with reference to the accompanying drawings in which.

Figure 1:
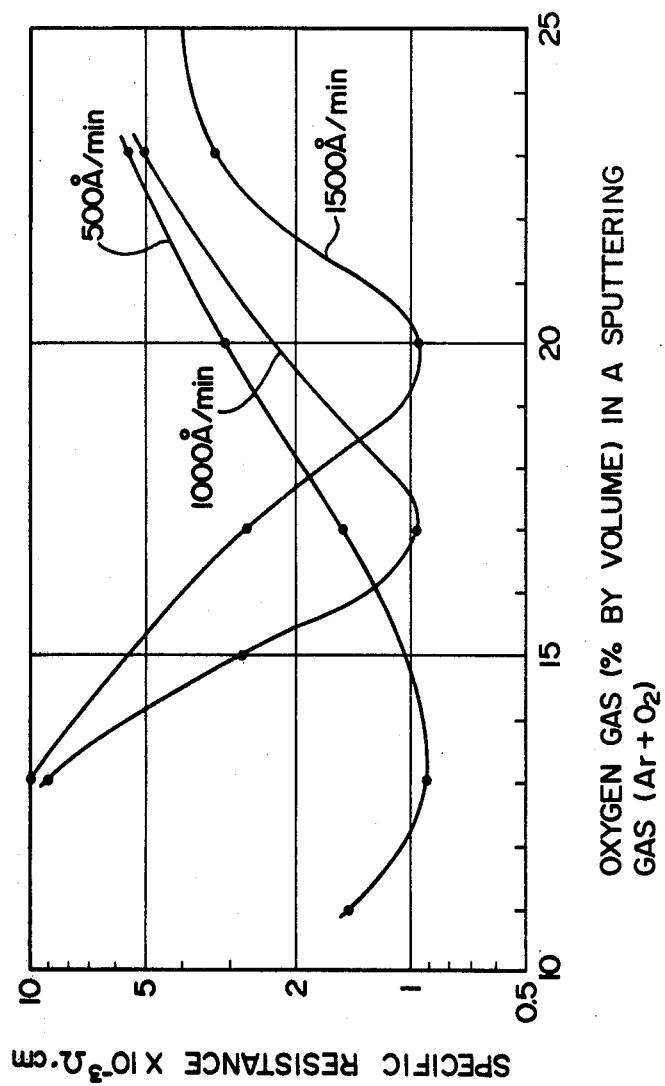
FIG. 1 is a diagram showing the relation between the specific resistance of an oxide coating formed on a support by the method of this invention and the composition of a sputtering gas, using the speed of forming the oxide coating as a parameter.

It is known that in the reactive sputtering technique, the application of a negative voltage to a target cathode results in a glow discharge, and a plasma is generated by the repetition of a process comprising the releasing of secondary electrons from the target upon the collision of the resulting positive ions with the target, the ionization of a sputtering gas by the collision of the secondary electrons with the sputtering gas and the releasing of secondary electrons from the target by the collision of the ions of the sputtering gas with the target. In the stage of plasma, atoms sputtered from the target and the sputtering gas receive energy from the plasma and form neutral atoms, ions, radicals, etc. Hence, in the plasma, a reaction involving the combination of the ions with the electrons to form neutral atoms, or a reaction involving changing of atoms in the exited state to those in the ground state takes place, and in the course of such a reaction, radiation having wavelengths inherent to the atoms or molecules in the plasma is generated.

The method of this invention first comprises a step of measuring at least one spectral component having a given wavelength of the spectrum of such plasma radiation.

Advantageously, the spectral component of a given wavelength should be that which has a wavelength inherent to the molecules, atoms, radicals, ions, etc. of the sputtering gas or an oxidizable substance constituting the target.

In the emission spectrum of a plasma, a very clear wavelength peak inherent to the substance that makes up the plasma exists. Hence, it is desirable to select such a wavelength peak as an object to be measured. Such emission spectra are known with regard to many substances. For example, from such emission spectra, the wavelength peak at 4511.323 Å for indium and peaks at 7503.867 Å and 7635.1 Å for oxygen may be selected for measuring purposes. The emission spectrum can be easily measured with regard to substances whose emission spectra are unknown, and therefore, it is not so difficult to determine a wavelength peak inherent to a particular substance.

The peak to be measured may be a peak derived from an oxidizable substance or a sputtering gas, or may be a plurality of peaks based on different substances.

The oxidizable substance convertible to an oxide may be an electrically conductive substance which can be used as a target in the reactive sputtering technique and can be combined with oxygen in a plasma to change to an oxide. Examples include metals of Groups II to VIII of the periodic table, preferably group IIb metals such as zinc and cadmium, group IIIb metals such as aluminum, gallium, indium and thallium, group IVb metals such as germanium and tin, group Vb metals such as antimony, group VIb metals such as tellurium, and group VIII metals such as ruthenium, rhodium and palladium. Of these, metals in the fifth period, above all cadmium, indium, tin and antimony, and alloys of these are especially preferred.

The support or substrate is preferably in the form of a film or sheet and may be made of, for example, a synthetic organic polymeric compound or glass. Examples of preferred synthetic organic polymeric compounds are acrylic resins, vinyl chloride resins, vinylidene chloride resins, polyethylene, and polyethylene terephthalate.

When a transparent or semi-transparent, preferably transparent, support is used, the resulting coated material can be advantageously used as an electrode of a liquid crystal display device. The transparent support preferably has a visible light transmittance of at least about 80%, and the semi-transparent support preferably has a visible light transmittance of less than about 80% but not less than about 40%.

The plate-like support preferably has a thickness of about 0.2 to about 8 mm, and the film-like support preferably has a thickness of about 0.02 to about 0.2 mm.

A mixture consisting substantially of oxygen gas and an inert gas well known in the reactive sputtering technique can be advantageously used as the sputtering gas. Examples of preferred inert gases are neon, argon, krypton and xenon. Argon is especially preferred. These inert gases may be used singly or as a mixture.

The mixing ratio of the oxygen gas to the inert gas is usually from 5:95 to 50:50, preferably from 5:95 to 20:80, by volume at 20° C. under 1 atmosphere.

The sputtering gas is introduced into the vacuum chamber at a flow rate of usually 0.05 to 1 cc/min., preferably 0.1 to 0.3 cc/min., per $cm^2$ of one surface of the target.

As stated hereinabove, the method of this invention is carried out by measuring the intensity (the quantity of light) of at least one spectral component having a specified wavelength of the spectrum of a plasma, comparing it with the predetermined standard intensity of a spectral component of the same wavelength and continuously or intermittently varying the physical amount of the sputtering gas and/or the amount of an electric current from a sputtering power supply so that the intensities of the two approach each other.

The intensity of at least one spectral component having a specified wavelength of the spectrum of the plasma is the intensity of a spectral component having at least one inherent wavelength on at least one component constituting the target or the sputtering gas. The physical amount of the sputtering gas to be varied is preferably the composition or flow rate of the sputtering gas.

Investigations of the present inventors have shown that the state of a plasma affects the electrical properties, transparency, crystallinity, adhesion (to the support), thickness, etc. of the oxide coating formed, and therefore, an oxide coating having a uniform thickness and uniform properties cannot be obtained by macroscopically observing the state of the plasma.

For example, oxygen defects existing in the oxide coating formed act as donors and supply free electrons. It is said therefore that the larger the number of the oxygen defects, the higher the conductivity of the coating, and that the smaller the number of the oxygen defects, the lower the conductivity of the oxide coating. In other words, to obtain an oxide coating having the desired electric conductivity, the number of oxygen defects existing in the resulting oxide coating should be controlled. If the proportion of oxygen in the sputtering gas is increased in an attempt to form an oxide coating having good electric conductivity, the surface of the target is oxidized to a greater extent by the collision of oxygen which has been activated in the plasma. Consequently, the speed of oxide coating formation decreases, and it is extremely difficult to obtain an oxide coating having constant and uniform properties.

FIG. 1 illustrates the fact discovered for the first time by the present inventors. It shows the results of reactive sputtering carried out at $3 \times 10^{-3}$ torr using an alloy consisting of 10% by weight of tin and 90% by weight of indium as a target. It is seen from FIG. 1 that the conductivity (specific resistance) of the resulting oxide coating depends not only upon the proportion of oxygen in the sputtering gas (a mixture of argon and oxygen), but also upon the speed at which the oxide coating was formed (500 Å/min., 1000 Å/min., and 1500 Å/min. shown in the diagram).

The fact that the specific resistance of the resulting oxide coating has a minimum value depending upon the proportion of the oxygen in the sputtering gas shows that the electric conductivity of the oxide coating obtained by the reactive sputtering technique does not simply vary depending upon the proportion of oxygen in the sputtering gas. It has been ascertained that the minimum value of the specific resistance shifts depending upon the speed of formation of the oxide coating, and in order to obtain an oxide coating having the highest possible conductivity by increasing the speed of formation, it is necessary to use a sputtering gas having a high oxygen content.

As stated hereinabove, the properties and thickness of the oxide coating formed correlate with each other and depend complexly upon the sputtering conditions. The present invention has made it possible to form easily an oxide coating having constant and uniform properties and thickness.

The method of this invention can be advantageously practiced by the apparatus of this invention.

The apparatus of this invention is the same as an ordinary reactive sputtering apparatus in that it comprises a vacuum chamber, a target electrode disposed within the vacuum chamber, means for introducing a sputtering gas into the vacuum chamber, means for discharging the sputtering gas from the vacuum chamber, and a power supply for applying a negative voltage to the target electrode. It is characterized by further including an optical spectroscopic instrument for measuring the intensity of at least one component having a given wavelength of the spectrum of a plasma formed on the surface of the target electrode, and control circuit means for comparing the measured intensity of the spectral component with the standard intensity of a spectral component having the same wavelength and, when there is a difference between the two, varying the physical amount of the sputtering gas and/or the amount of an electric current from the sputtering power supply so that the measured intensity approaches the standard intensity.

The optical spectroscopic instrument is preferably comprised of a spectroscope and a light quantity detector, and the light quantity detector is preferably a photo-multiplier tube.

Preferably, the sputtering apparatus of this invention has a window protruding from the vacuum chamber and a light-collecting device provided opposite to the window independently of the vacuum chamber. Preferably, the protruding window has provided within the protruding section a plurality of slender tubes aligned in the direction which does not obstruct the field of vision. The protruding window and the slender tubes are effective for preventing clouding of the window, and permit easy observation and measurement of the plasma radiation through the window. The light-collecting device is preferably equipped with a chopper, and connected to the spectroscopic instrument through optical fibers.

The sputtering apparatus of this invention may have a magnet at that surface of the target which does not face the support. Since the magnetic lines of force generated from the magnet capture the plasma in the vicinity of the target, the degree of pressure reduction within the vacuum chamber can be increased to about $10^{-3}$ when the apparatus has a magnet. This results in lengthening of the mean free path of an ion in the plasma, and the efficiency of sputtering is increased. When the apparatus does not include a magnet, the plasma spreads within the vacuum chamber. Accordingly, the degree of pressure reduction must be adjusted to about $10^{-2}$ torr, for example. As a result, the mean free path of an ion in the plasma correspondingly becomes shorter, and the efficiency of sputtering decreases accordingly.

With reference to FIGS. 2 to 6, the present invention will be further described.

Figure 2:
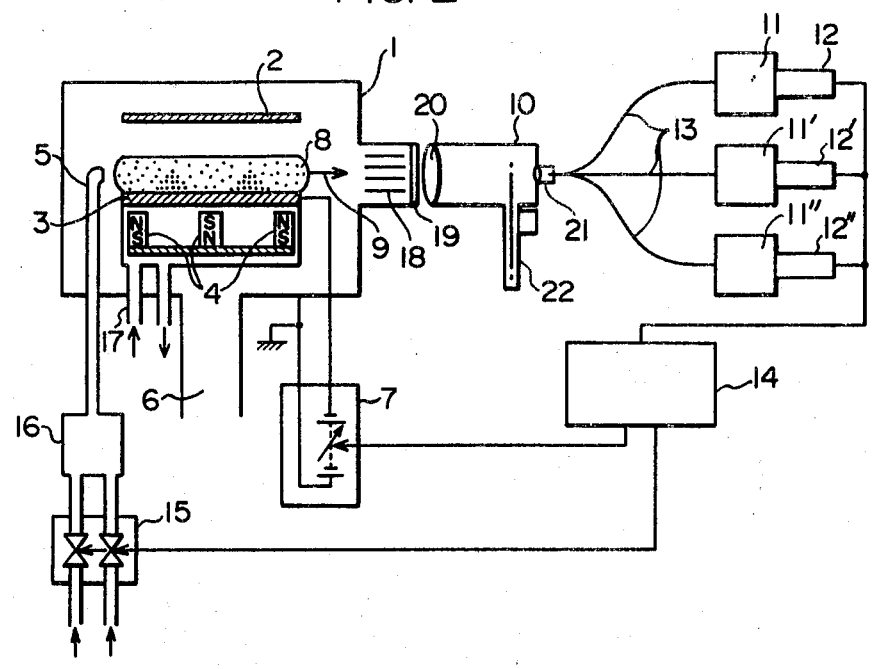
FIG. 2 is a schematic view showing one example of the sputtering apparatus of the invention.

FIG. 2 is a schematic view of the sputtering apparatus of this invention including a vacuum chamber 1 with a support 1 placed therein, a target 3 as a cathode, a magnet 4, an inlet port 5 for introducing a sputtering gas into the vacuum chamber 1, a discharge port 6 for discharging the sputtering gas, a sputtering power supply 7 (a power supply for generation of a plasma) for generating a plasma 8 with plasma radiation 9, a light-collecting device 10, spectroscopes 11, 11' and 11", light quantity detectors 12, 12' and 12", optical fibers 13, a control circuit device 14, a device 15 for introducing the sputtering gas, a sputtering gas mixing box 16, a water-cooling pipe 17 for cooling the target 3, a window 18, slits 18 for preventing clouding of the window 19, a plasma radiation collecting lens 20, a lens 21 for introducing the plasma radiation into the optical fibers 13, and a chopper 22.

The vacuum chamber 1 is evacuated by an evacuating device (not shown) through the sputtering gas discharging port 6. With evacuation, a sputting gas such as a mixture of oxygen and an inert gas such as argon is introduced from the sputtering gas inlet port 5. The sputtering gas is obtained by introducing, for example, argon and oxygen in a volume ratio of 4:1 by the gas introducing device 15 and mixing them in the gas mixing box 16. The pressure of the gas within the vacuum chamber is set at a pressure suitable for reactive sputtering, for example at an equlibrium pressure of $3 \times 10^{-3}$ torr.

Then, by the power supply 7 whose positive pole is connected to the vacuum chamber 1, a negative voltage of, for example, 330 V is applied to the target 3 (e.g., made of an alloy consistng of 10% by weight of Sn and 90% by weight of In). The plasma 8 is generated and confined by the magnetic field of the magnet 4. In the plasma, an oxidizable substance sputtered from the target 3, for example In and Sn, and the sputtering gas (e.g., a mixture of argon and oxygen) gain energy from the plasma to form atoms or molecules of the oxidizable substance and the sputtering gas or their ions and radicals, and emit plasma radiation having wavelengths inherent thereto.

The plasma radiation 9 is collected by light-collecting lens 20 and dispersed by the spectroscopes 11, 11' and 11". The quantities of light at wavelengths inherent to the individual components of the spectrum of the plasma are measured by the light quantity detectors 12, 12' and 12". The inherent wavelengths and the quantities of light so measured are then fed into the control circuit device 14.

For example, the quantity of light at a wavelength of 4511.323 Å inherent to indium in the plasma spectrum is measured by the detector 12; the quantity of light at a wavelength of 7503.867 Å inherent to argon in the plasma spectrum is measured by the detector 12'; and the quantity of light at a wavelength of 7771.928 inherent to oxygen in the plasma spectrum is measured by the detector 12". In this way, the quantities of light of spectral components based on different components of the plasma spectrum are measured by the light quantity detectors. The above sputtering apparatus having the three spectroscopes 11, 11' and 11" and the three light quantity detectors 12, 12' and 12" for measuring the quantities of light based on the three different components in the plasma spectrum is only an example, and may include one, two, or more than 4, spectroscopes or light quantity detectors.

It will be easily understood that even when the method of this invention is performed by using the sputtering apparatus of this invention including a plurality of each of the spectroscopes and light quantity detectors, only some of them may be used instead of operating all of them.

Wavelengths inherent to specified components of a plasma spectrum and the quantities of light at these wavelengths are stored in advance in the control circuit device 14. The control circuit device 14 compares the quantity of light at a specified wavelength fed thereinto with the memorized standard quantity of light, and when there is a difference between the two quantities, sends a control signal to the sputtering gas introducing device 15 and/or the plasma generatng power supply 7 causing them to vary the physical amount of the sputtering gas and/or the amount of a current from the sputtering power supply.

For example, when the quantity of light at a wavelength inherent to In or the quantity of light at a wavelength inherent to Ar is smaller than the quantities of light having the same wavelengths which are stored in the control circuit device 14, the control circuit device 14 sends to the power supply 7 a control signal for increasing the voltage of the power supply 7 thereby to increase the speed of sputtering. If the former is larger than the latter, the control circuit device 14 sends a control signal for decreasing the voltage of the power supply 7 to the power supply 7, thereby to decrease the speed of sputtering. Furthermore, if the quantity of light at a wavelength inherent to oxygen or the quantity of light at a wavelength inherent to Ar is smaller than the quantity of light at the same wavelength which is stored in the control circuit device 14, the control circuit device 14 sends to the sputtering gas introducing device 15 a control signal for opening a valve for $O_2$ or Ar. If the former is larger than the latter, the control circuit device 14 sends a control signal for closing the valve for $O_2$ or Ar to the gas introducing device 15. Thus, automatic control is effected so as to maintain the quantity of the resulting oxide coating constant.

Figure 3:
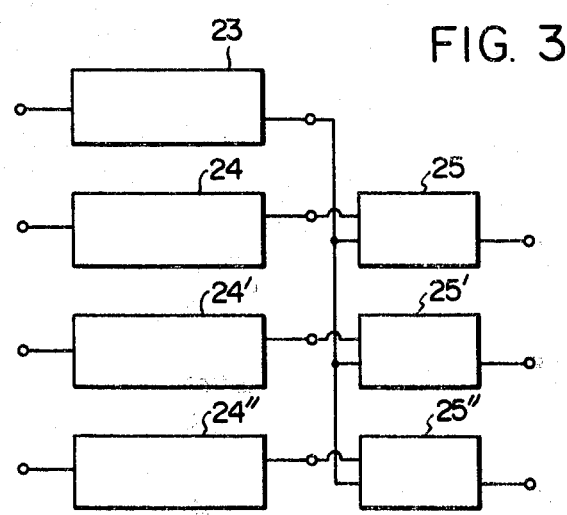
FIG. 3 is a view of one example of a control circuit device to be incorporated in the sputtering apparatus of the invention.

FIG. 3 shows the construction of the control circuit device 14. As shown, the control circuit device 14 is comprised of a device 23 for measuring a sputtering current signal, light signal measuring devices 24, 24' and 24'', an operating, comparing, and control signal producing unit 25, 25' and 25''.

When the light signal measuring unit 24 is to measure a light signal based on a constituent element (an oxidizable substance such as In) of the target 3, the free terminal of the signal output unit 25 is connected to the sputtering power supply 7. When the light signal measuring units 24' and 24'' are to measure signals based on different components (e.g., Ar and O) of the sputtering gas, the free terminals of the signal output units 25' and 25'' are connected respectively to the gas (e.g., argon and oxygen) flow rate controlling input terminals of the sputtering gas introducing device 15.

Figure 4:
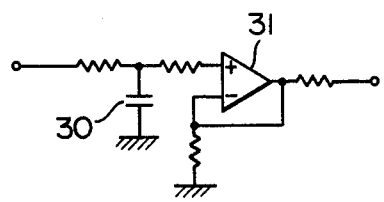
FIG. 4 is a circuit diagram of a sputtering current signal measuring device in the aforesaid control circuit device.

FIG. 4 is a circuit diagram for the sputtering current signal measuring device 23. In FIG. 4, the reference numeral 30 represents a condenser and 31, an ic. The free terminal at the left end in FIG. 4 is connected to the current input terminal of the sputtering power supply 7, and from there, a voltage signal proportional to the sputtering current is fed (see the above description with reference to FIG. 3). The condenser 30 cuts high-frequency noises of the fed current signal. The fed current signal is amplified to a desired voltage signal by the ic 31, and taken out from the free terminal at the right end in FIG. 4.

Figure 5:
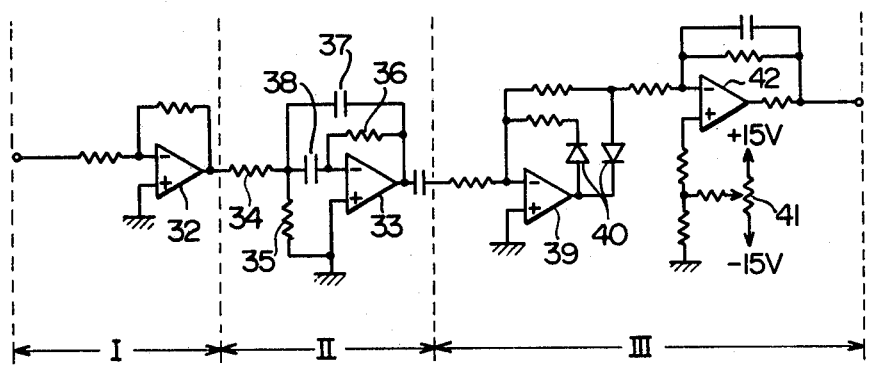
FIG. 5 is a circuit diagram of a light signal measuring device in the aforesaid control circuit device.

FIG. 5 is a circuit diagram for the light signal measuring units 24, 24' and 24''. In FIG. 5, circuit sections I, II and III respectively represent a current-voltage converter circuit, a filter circuit and a rectification output circuit. The reference numerals 32, 33, 39 and 42 represent an ic; 34, 35 and 36, resistors; 37 and 38, condensers; 40, a diode; and 41, a variable resistor.

The free terminal at the left end in FIG. 5 is connected to the output terminals of the light quantity detector 12, 12' or 12'', and a light quantity signal from the detector 12, 12' or 12'' is fed from it as a current signal. The fed current signal is converted into a voltage signal by the ic 32 and fed into the filter circuit. The filter circuit II is comprised of the ic 33, the resistors 34, 35 and 36 and the condensers 37 and 38 to form a band path filter. It selects a signal of the chopping frequency of the chopper 22 (see FIG. 2) and feeds an electrical signal to the rectification output circuit III. The rectification output circuit rectifies the input electrical signal of an alternate current by means of the ic 39 and the diode 40, amplifies it at the ic 42, and sends it from the free terminal at the right end in FIG. 5.

The adjustment of the zero output in the absence of a light signal fed into the light quantity detectors 12, 12' and 12'' can be effected by means of the variable resistor 41.

Figure 6:
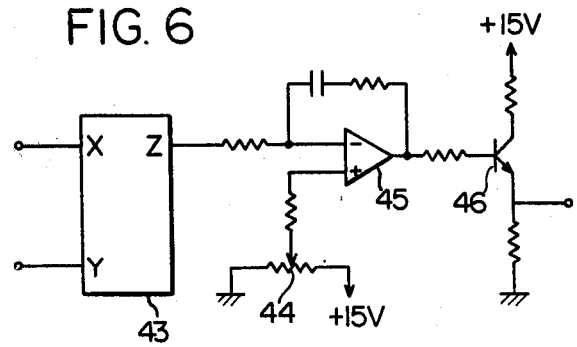
FIG. 6 is a circuit diagram for an operating, comparing and control signal producing device within the control circuit device.

FIG. 6 shows a circuit diagram of the operating, comparing and control signal producing devices 25, 25' and 25''. In FIG. 6, the reference numeral 43 represents a division operating element (ic) which produces a signal of $z=x/y$. The reference numeral 44 represents a volume; 45, an ic; and 46, a transistor. The free terminal at the left top end in the drawing is connected to an electrical signal output terminal from which an electrical signal is fed. The free terminal at the left bottom end in the drawing is connected to the sputtering current signal output terminal from which a sputtering current signal is fed. The volume 44 feeds a preset value $V_R$ of the intensity of a light signal corresponding to the desired standard quantity of light into the ic 45. On the other hand, a light signal intensity $V_Z$ from the ic 43 is fed into the ic 45. Thus, the ic 45 sends a voltage proportional to the value of $V_Z - V_R$ to the base of the transistor 46. The transistor 46 is a transistor for output power which sends a controlled voltage from the free terminal at the left end in FIG. 6 so that the value of $V_Z - V_R$ equals zero.

Thus, according to this invention, the detection and controlling of a plasma condition are automated and an oxide coating can be formed under pre-set reactive sputtering conditions. Since the reactive sputtering in accordance with the invention can be practiced by computerized control according to a series of programs from the evacuation of the vacuum chamber to the completion of the oxide coating formation, it can always give an oxide coating having a uniform and constant quality.

The present invention has thus established quantification of the state of oxide coating formation by the detection of the emission spectrum of a plasma. This brings about the result that an oxide coating can be formed more stably than by conventional methods. The industrial utility of the invention is therefore great.

The following Example shows that the present invention can give an oxide coating having excellent properties and a uniform thickness.

EXAMPLE

In each run, an oxide coating was formed on a support by using the sputtering apparatus shown in FIG. 1 including the control circuit device shown in FIG. 2 comprised of the circuits shown in FIGS. 3 to 5.

Each of the indium-tin alloys and indium-tin-antimony alloys indicated in Table 1 was used as a target, and a glass plate was used as the support. The sputtering gas used was a mixture of argon and oxygen.

Wavelengths of 4511.323 Å (inherent to indium), 7503.867 Å (inherent to argon) and 7771.928 Å (inherent to oxygen) in the spectrum of the generated plasma were respectively selected by spectroscopes 11, 11' and 11'', and the quantities of light at the respective wavelengths were measured by light quantity detectors (photomultiplier tubes) 12, 12' and 12''. Electrical signals corresponding to the respective light quantities were fed into the light signal measuring devices 24, 24' and 24''. In the operating, comparing, and control signal producing devices 25, 25' and 25'' respectively, the input electrical signals corresponding to the light quantities were divided by the amount of the electric current, the quotient was compared with the standard value, and a control signal based on the comparison was produced. By continuously operating the sputtering gas introducing device and the sputtering power supply, the composition of the sputtering gas and the amount of the electric current from the power supply were continuously varied. The results are shown in Table 1.

Specifically, a gaseous mixture of argon and oxygen in a volume ratio of 50:50 was introduced into the vacuum chamber, and the sputtering conditions were adjusted so that the speed of forming the oxide coating was about 100 Å and the values of $I_{7504}/J$ and $I_{7772}/J$ were both 50:50.

Then, by using the apparatus in which the above adjustment was effected, a gaseous mixture of argon and oxygen in a volume ratio of from 80:20 to 90:10 was introduced into the vacuum chamber. The current from the sputtering power supply was adjusted and the sputtering was carried out so as to provide the speeds of forming oxide coatings as shown in Table 1. The support (glass plate) was moved over the target at a speed of about 400 mm/min.

Table 1 shows the compositions of the targets used, the sputtering conditions and the properties of the coatings formed.

In Table 1, $I_{4511}$ is the quantity of light having a wavelength of 4511.323 Å in (In) the spectrum of the plasma; $I_{7504}$, the quantity of light having a wavelength of 7503.867 Å (Ar) in the spectrum of the plasma; $I_{7772}$, the quantity of light having a wavelength of 7771.928 Å (oxygen); and J, the sputtering current. The value of $I_{4511}/J$ is proportional to the speed of formation of an oxide coating on the support, and the values of $I_{7504}/J$ and $I_{7772}/J$ are proportional respectively to the concentration of the argon gas in the plasma and the concentration of the oxygen gas in the plasma.

TABLE 1

| Target composition (weight %) | | | Sputtering conditions | | | | Properties of the oxide coating formed | |
|---|---|---|---|---|---|---|---|---|
| | | | Degree of vacuum ($\times 10^{-3}$ torr) | Standard light intensity | | | Speed of forming the oxide coating (A/min.) | Thickness [$(\bar{d}) \pm \Delta d$; Å] | Specific resistance [$(\bar{\rho}) \pm (\Delta\rho)$; $\times 10^{-4}$ ohm-cm] |
| In | Sn | Sb | | $I_{4511}/J$ | $I_{7504}/J$ | $I_{7772}/J$ | | | |
| 95 | 5 | 0 | 3 | 250 | 87 | 13 | 1250 | 249 ± 4 | 9.1 ± 0.7 |
| 92.5 | 7.5 | 0 | 3 | 250 | 87 | 13 | 1300 | 258 ± 9 | 6.0 ± 0.3 |
| 90 | 10 | 0 | 3 | 250 | 87 | 13 | 1350 | 269 ± 15 | 6.7 ± 0.5 |
| 90 | 10 | 0 | 2.5 | 250 | 86 | 14 | 1250 | 259 ± 10 | 6.3 ± 0.2 |
| 90 | 10 | 0 | 2 | 250 | 85 | 15 | 1300 | 257 ± 12 | 6.5 ± 0.3 |
| 85 | 15 | 0 | 3 | 250 | 87 | 13 | 1450 | 286 ± 11 | 9.4 ± 0.4 |
| 90 | 9 | 1 | 3 | 300 | 85 | 15 | 1550 | 310 ± 14 | 7.8 ± 0.8 |
| 90 | 7 | 3 | 3 | 300 | 85 | 15 | 1500 | 303 ± 8 | 9.0 ± 0.7 |

In Table 1, the thickness and specific resistance of the oxide coating are shown by average values ($\bar{d}$) and ($\bar{\rho}$) of ten replicates and standard deviations ($\Delta d$) and ($\Delta\rho$).

What we claim is:

1. In a method for forming a coating of an oxide on a support by the reactive sputtering technique, the improvement which comprises measuring the optical intensities of three spectral components having a given wavelength of the spectrum of a plasma formed between the support and a target composed of an oxidizable substance convertible to said oxide, said three spectral components being derived from an inert gas, oxygen gas and said oxidizable substance, comparing the measured intensities of the three spectral components with the standard intensities of three spectral components of the same wavelength respectively, and continuously or intermittently varying the physical amount of a sputtering gas and the amount of an electric current from a sputtering power supply so that the measured intensities of the former spectral component approach the standard intensities of the latter spectral components.

2. The method of claim 1 wherein the oxidizable substance constituting the target is a metal of Groups II to VIII of the periodic table.

3. The method of claim 1 or 2 wherein the oxidizable substance is cadmium, indium, tin, antimoy, or an alloy thereof.

4. The method of claim 1 wherein the support is in the form of a film or sheet.

5. The method of claim 1 wherein the support is made from a synthetic organic polymeric compound or glass.

6. The method of claim 1 wherein the support is transparent or semi-transparent.

7. The method of claim 1 wherein the sputtering gas is composed substantially of oxygen and at least one inert gas selected from neon, argon, krypton and xenon.

8. The method of claim 1 wherein the physical amount of the sputtering gas is the composition or flow rate of the gas.

9. In a sputtering apparatus comprising a vacuum chamber, a target electrode disposed within the vacuum chamber, means for introducing a sputtering gas into the vacuum chamber, means for discharging the sputtering gas from the vacuum chamber, and a power supply for applying a negative voltage, the improvement wherein the apparatus further includes an optical spectroscopic instrument for measuring the optical intensities of three components having a given wavelength of the spectrum of a plasma formed between the support and a target composed of an oxidizable substance convertible to said oxide, said three spectral components being derived from an inert gas, oxygen gas and said oxidizable substance, and control circuit means for comparing the measured intensities of the three spectral components with the standard intensities of three spectral components having the same wavelength respectively and when there is a difference between the measured intensity and the standard intensity, varying the physical amount of the sputtering gas and the amount of an electric current from the sputtering power supply so that the measured intensity approaches the standard intensity.

10. The apparatus of claim 9 wherein the spectroscopic instrument is comprised of a spectroscope and a light quantity detector.

11. The apparatus of claim 10 wherein the light quantity detector is a photomultiplier tube.

12. The apparatus of claim 9 or 11 wherein the vacuum chamber has a window protruding therefrom for observing the plasma radiation, and a light-collector is provided opposite to the window independently of the vacuum chamber.

13. The apparatus of claim 12 wherein said window has provided at its protruding section a plurality of slender tubes aligned in a direction which does not obstruct vision.

14. The apparatus of claim 12 or 13 wherein the light collector has a chopper.

15. The apparatus of claim 12 wherein the light collector is connected to the spectroscopic instrument through optical fibers.

* * * * *